United States Patent [19]

Barbour et al.

[11] Patent Number: 5,986,174
[45] Date of Patent: Nov. 16, 1999

[54] MAIZE PROMOTER SEQUENCE FOR LEAF- AND STALK-PREFERRED GENE EXPRESSION

[75] Inventors: Eric Barbour, Des Moines; Chris L. Baszczynski, Urbandale, both of Iowa; Jeffrey L. Rosichan, Burnsville, Minn.; Jeanine Horowitz, Coral Gables, Fla.

[73] Assignee: Pioneer Hi-Bred International, Inc., Des Moines, Iowa

[21] Appl. No.: 08/667,809

[22] Filed: Jun. 21, 1996

[51] Int. Cl.$^6$ .............................. C12N 15/82; C12N 5/04; C12N 15/29

[52] U.S. Cl. ........................ 800/287; 435/410; 435/412; 435/416; 435/418; 435/419; 536/23.1; 536/24.1; 800/279; 800/287; 800/295; 800/300; 800/301; 800/320.1

[58] Field of Search ................................. 536/24.1, 23.1; 800/205, 250, DIG. 56, 278, 279, 287, 295, 298, 300, 301, 320.1; 435/410, 412, 416, 418, 419

[56] References Cited

FOREIGN PATENT DOCUMENTS 0 452 269 A2  10/1991  European Pat. Off. .
WO 93/18169    9/1993   WIPO .

OTHER PUBLICATIONS

Matsuoka, et al. (1993). Proc. Natl. Acad. Sci. USA., 90: 9586–9590, "Tissue–specific light–regulated expression directed by the promoter of a $C_4$ gene, maize pyruvate, orthophoshate dikinase, in a $C_3$ plant, rice".

Baysdorfer, et al. (1996). Embl. Sequence Database, XP 0020779112, "zEST00814 Maize leaf zea Mays cDNA clone 5'end".

Lee, et al. "Positive selection of candidate tumor–suppressor genes by subtractive hybridization." 1991. *Proc. Natl. Acad. Sci. USA*, 88:2825–2829.

Berchtold, M.W. 1989. "A simple method for direct cloning and sequencing cDNA by the use of a simgle specific oligonucleotide and oligo(dT) in a polymerase chain reaction." *Nuc. Acids Res.* 17: 453.

Liang and Pardee. 1992. "Differential display of eukaryotic messenger RNA by means of the polymerase chain reaction." *Science*, 257: 967–971.

Alwine, et al. 1977. "Method for detection of specific RNAs in agarose gels by transfer to diazobenzyloxymethyl–paper and hybridization with DNA probes." *Proc. Natl. Acad. Sci. USA*, 74: 5350–5354.

Koziel, et al. 1993. "Field performance of elite transgenic maize from plants expressing an insecticidal protein derived from *Bacilus thurigiensis*." *Bio/Technology* 11: 194–200.

Depicker, et al. 1982. "Nopaline synthase: transcript mapping and DNA sequence." *J. Mol. Appld. Genet.* 1: 561–573.

Christensen, et al. 1992, "Maize ubiquitin genes: structure, thermal perturbation of expression and transcript splicing, and promoter activity following transfer to protoplasts by electroporation." *Plant Mol. Biol.* 18: 675–689.

Odell, et al. 1985. "Identification of DNA sequences required for activity of the cauliflower mosaic virus 35S promoter." *Science* 313: 810–812.

Showers, et al. 1989. "European Corn Borer. Development and Management." North Central Regional Extension Publication Number NCR327. Printed and distributed in cooperation with Extension Service, U.S. Department of Agriculture, Washington, DC.

Mariani, et al. 1990. "Induction of male sterility in plants by a chimaeric ribonuclease gene." *Nature*, 347: 737–741.

Boutilier, et al. 1994. "Expression of the BnmNAP subfamily of napin genes coincides with the induction of *Brassica microspore embryogenesis*. " *Plant Molec. Biol.* 26: 1711–1723.

Wessler, S.R. 1994. "Isolation of RNA from Wx and wx endosperms." In *The Maize Handbook,* M.Freeling and V. Walbot eds. Springer–Verlag, New York. pp. 545–546.

Sanger, et al. 1977. "DNA sequencing with chain–terminating inhibitors." *Proc. Natl. Acad. Sci. USA,* 74: 5463–5467.

Budelier, et al. 1990. "Regulation of a stylar transmitting tissue–specific gene in wild–type and transgenic tomato and tobacco." *Mol. Gen. Genet.* 224: 183–192.

Ni–Gruk, et al. 1980. "In vitro 32P–labelling of viroid RNA for hybridization studies." *J. Virol. Meth.* 229: 229–234.

Kim et al. Plant Molecular Biology. 1994. vol. 24: 105–117.

Short Protocols in Molecular Biology. Greene Publishing Associates and Wiley–Interscience. John wiley & Sons. 1989.

Napoli et al. The Plant Cell. 1989. vol. 2: 278–289.

Fromm et al. Bio/Technology. 1990. vol. 8: 833–839.

Gordon–Kamm et al. The Plant Cell. 1990. vol. 2: 603–618.

McBride et al. Bio/Technology. 1995. vol. 13: 362–365.

*Primary Examiner*—Lynette R. F. Smith
*Assistant Examiner*—Ousama Zaghmout

[57] ABSTRACT

This invention relates generally to mechanisms of gene expression in plants and more specifically to regulation of expression of genes in plants in a "tissue-preferred" manner. Regulation of expression is achieved using a transcriptional regulatory unit capable of driving expression of genes within certain tissues of a plant. Said transcriptional regulatory unit are to be utilized for driving expression of genes effective in the control of insect or other pests which threaten plants.

12 Claims, 7 Drawing Sheets

```
                                                                    GRP 90    ⎤
                                                                    HOMOLOGUE ⎬
                                                                    SEQUENCE  ⎦
EcoR1
GAATTCCGTTC CTG TCG GAC TGG TGG AAG AAG GCC CTG GAG AGC GAG AAC GTG GAC  ⎤
            Leu Ser Asp Trp Trp Lys Lys Ala Leu Glu Ser Glu Asn Val Asp
TCG GTG AAG ATC AGC AAC CGG CTG CAC GAC ACC CCC TGC GTC GTG GTC ACC TCC
Ser Val Lys Ile Ser Asn Arg Leu His Asp Thr Pro Cys Val Val Val Thr Ser  ⎦
AAG TAC GGG TGG AGC GCC AAC ATG GAG AAG ATC ATG CAG GCG CAG ACC CTG TCG
Lys Tyr Gly Trp Ser Ala Asn Met Glu Lys Ile Met Gln Ala Gln Thr Leu Ser
GAC TCG AGC AAG CAG GCG TAC ATG CGC GGC AAA GAGGGCCTCTCGATCGCTCATCAGTCGC
Asp Ser Ser Lys Gln Ala Tyr Met Arg Gly Lys  ◄———SDP
CAGAGGAGTAGTTGATCGAGGTGAGTGAGGTTGAAAAGCAGGCGGCGAACAAAGGCACCATCGTC ATG
                                                                   MET
GAC GGC GGA TAC TAC GGC GGC CGC GAT CAG CGC TAC AGC GGC GGG TAC TAC GGC
Asp Gly Gly Tyr Tyr Gly Gly Arg Asp Gln Arg Tyr Ser Gly Gly Tyr Tyr Gly
GGC GGT GGC ATC GCG ACG CCG GGG TAC GCT CCG GCG GTC CCG TAC GGG ATG TCG
Gly Gly Gly Ile Ala Thr Pro Gly Tyr Ala Pro Ala Val Pro Tyr Gly Met Ser
CAG GTG AAC ATC GAG GGC AAC GGG TGC GGG CGG CGG CTG CCG CCG CAG CCG ACC
Gln Val Asn Ile Glu Gly Asn Gly Cys Gly Arg Arg Leu Pro Pro Gln Pro Thr
GTG AAG GTG TAC TGC CGC GCC AAC CCC AAC TAC GCC ATG AGC GTC CGC GAC GGG
Val Lys Val Tyr Cys Arg Ala Asn Pro Asn Tyr Ala Met Ser Val Arg Asp Gly
AAG GTG GTG CTG GCG CCG GCG AAC CCC AAG GAC GAG TAC CAG CAC TGG ATC AAG
Lys Val Val Leu Ala Pro Ala Asn Pro Lys Asp Glu Tyr Gln His Trp Ile Lys
GAC ATG CGG TGG AGC ACG AGC ATC AAG GAC GAG GAA GGT TAC CCG GCG TTC GCG
Asp Met Arg Trp Ser Thr Ser Ile Lys Asp Glu Glu Gly Tyr Pro Ala Phe Ala
CTG GTG AAC AAG GCG ACC GGG GAG GCC ATC AAG CAC TCG CTG GGG CAG TCC CAC
Leu Val Asn Lys Ala Thr Gly Glu Ala Ile Lys His Ser Leu Gly Gln Ser His
CCG GTG CGC CTG GTG CCC TAC AAC CCG GAC TTT TTG GAC GAG TCG GTG CTG TGG
Pro Val Arg Leu Val Pro Tyr Asn Pro Asp Phe Leu Asp Glu Ser Val Leu Trp
ACG GAG AGC CGC GAC GTC GGC AAC GGC TTC CGC TGC GTC CGC ATG GTC AAC AAC
Thr Glu Ser Arg Asp Val Gly Asn Gly Phe Arg Cys Val Arg Met Val Asn Asn
ATC TAC CTC AAC TTC GAC GCC CTC CAC GGC GAC AAG TGG CAC GGC GGC GTC CGT
Ile Tyr Leu Asn Phe Asp Ala Leu His Gly Asp Lys Trp His Gly Gly Val Arg
GAC GGC ACC GAC GTC GTG CTC TGG AAG TGG TGC GAG GGC GAC AAC CAG CGC TGG
Asp Gly Thr Asp Val Val Leu Trp Lys Trp Cys Glu Gly Asp Asn Gln Arg Trp
AAG ATC CAG CCC TAC TAC TGA ACCAACGGATGATATGACCATCGCGCCCATCGATCGTGCACATG
Lys Ile Gln Pro Tyr Tyr • • •
CATGCATACGTACTAGCAGAATAACAGGGGTCTTATCTCCCGAGGCGTCTTTTGCATGCATGCCAGCAGTTG
CATAGATAAAGCAGGAGCGAGACAAAGGGTGTTCATGTATATTGCAGCTGATCACTGTATGTATGTGCCAT
                                                          Poly A Tail    Xbal  SalI
TGTGCCTTGTAATAATACATATAATAATAAAGTTGCTCGGAAAAAAAAAAAAAAAAAAAAAAATCTAGAGTCG
  PstI       Hind III
ACCTGCAGCCCAAGCTTGTATTCTATAGTGTCACCTAAA                           MS8-15   ⎤
                                                                  cDNA     ⎬
                                                                  SEQUENCE ⎦
```

FIG. 2

```
TACCGGGCCC CCCCTCGAGG TCGACGGTAT CGATAAGCTT GATATCGAAT TCTAACTCAA
ACGAACATGC CCTTATCGAT TTAGCTAGAG AGATGCGAGG AAAACTCTTA TTAGTATTGT
TGCTTTGGTG GTGGCGTAGA TAAAATAGAG CAAATAGAAA GGCACATCAG AGGTGGCACT
GGAGACGATG TTGACAGTGG CGTCGCACTT CCTCTCGAAG CTCGACCATG CCTGGCAGCA
CAACGTGTAT GACCCGCATG ACGCCCTCGA CGTTGACCTA GATCAGTTGC GCAGCAGCTC
CTCATCCACC CCGTGCCAGT CGTGCGCGTA CGGATAAGAC AACCCATCAT AGCCATGGAT
GGAGTCTCGA GCATCTCGAC GCCGGCCACC AGCCCCTCGA GATCCTTGCT GGAGGCGCGG
GCGTCGAGGA GGAGGAGATG GGCGAAGGTG AGGGAGGGGA CCAAGGGGGT CTATCGCGGT
AGGACAGGGG GCCAGGAAGG CAGGGCAAC  ACATGGGGC  AGCACAAGCA GGGGCCGGAG
TGGAGGGAGG CAAGGATGGT AGGCGTTTGG CGTCGCGAAG GAGGCGAGGA GCGCGGTGCA
GCGGTGCATG GAACGCGGGA TGGGCTTGCG ACTGACGATG GCGTGGAGGG ACGACATCAG
TATAGATGGC CAAATGGGTC GTACCTATCA GACTGGCCTG AAGTACGAAC CATTTAATAG
TGTCGTGGCC CAACCTGACA TTATTAAAAT GGGCTCGTGC CAGCACGGCA CGAGAGGCGT
GCCATGCTTG AGCCGTTGTC TCGGCCCGTA GTGCCGGTTT GGCCTAATAT GATTATTTTT
TTATTATTTT GAAAACTCAG CCGACACATA TTTATAACAC CTATTGACTA TTAGGCACAA
ACTTGATTGG GCTCAAGTGG GTAGCAGAGC ATAGTCAGTG TCTGTTGCCT TTACCAAGGC
GCACGGGTTT GATCCCCCTC CCTGCGCTAT AATTTTGGAC TATTTTTCTA TAGGCGTCGA
GACGAAGCAT GATTCCACCA GTGATCTACA CTATTATCTT AATATGTAGT AGAGATAGAG
ATTTTATAGA TTCAGACCCC TAAACCTTTA ATGAGATTAT TTTTCTCAGC TACTCAAATA
                                           ────────▶ Repeat 3
AAGGGGAGAA CTCTCCTCCC CAATTAACCG TTTTTTTCTT CATATTTTCT ACACTACATA
TGCCTAAAAT AAATAATTGA GAGATGAGTT AAGAGAAAGA AAAGGTAATG TATAATGCTG
GTTTTCAGGA TGGTTGGTTT TAAGATCTAA TTGTTATTAT TCACCGCCTA AACGAACCTT
TAAAATAAGA CATAACACAG CTCCTTAATT TCTCATTGGG CATGGAGTTT TCTTGTTTTG
CTGGAGAGAA AGAAGACCTT TGAAATTTCA AAACACTCTT TTGTGGCTAG TTTGAAAACT
CGAATCATCT CCAGGATCGA CCGGAATTAG GGAATAAATA AACTATTTTT TCTCTCAATC
                                           ────────▶ Repeat 2
TCAAAGACAA TTTAAGTTTC CAAACTAGCG ATTAATCTTA ACCAATGACT AGACTTTGTG
TTGGTTTTTT CTCTTACTGC TGGAGATGCT AAGGATTCTT CTTCCAAGAA CGACTAGAAA
      ────────▶ Repeat 1
CCGAATCGCT TTTTCCCTCG GCTAGTTTCG CATGGCATCG TCCTTCCTGC CCATGCGCGC
ACAACCATCC ATCCACTGAC GATGCGATGC CTACCCACCA CCTCGCGCAG CGTGATGCTA
                         ─────────────▶ CTF/NF1 BINDING SITE
ACGCCACCAC ATGCACCACC AGTGGGGCAG CTGGGGACGC CGGGAGCAAC CGGCAGCGCC
CTATAAATCT GCCGGCCCGG CCGTTGCATT GTCTGCGTCA GGGCCTCTTG ATCATCAGTC
   ─────▶ TATA BOX                                    ◀─── SDP
GCCAGAGGAG CTGTTGATCG AGGTGAGTGA GGTTGAAAAG CAGGCGGCGA ACAAAGGCAC
              ────────▶ PUTATIVE CAP SITE
CATCGTC ATG GAC GGC GGA TAC TAC GGC GGC CGC CAC CGC GGT GGA GCT CCA
        Met Asp Gly Gly Tyr Tyr Gly Gly Arg His Arg Gly Gly Ala Pro
GCT TTT GTT CCC TTT AGT GAG GGT T
Ala Phe Val Pro Phe Ser Glu Gly
```

FIG. 3

```
         HincII
         HpaI
   1 CCGGTTAACT CTAGAGGGTA GCAGAGCATA GTCAGTGTCT GTTGCCTTTA CCAAGGCGCA
     ─────────────────────────────────────────▶
                       ────────── DO2461
  61 CGGGTTTGAT CCCCCTCCCT GCGCTATAAT TTTGGACTAT TTTTCTATAG GCGTCGAGAC
 121 GAAGCATGAT TCCACCAGTG ATCTACACTA TTATCTTAAT ATGTAGTAGA GATAGAGATT
 181 TTATAGATTC AGACCCCTAA ACCTTTAATG AGATTATTTT TCTCAGCTAC TCAAATAAAG
                                                ──────▶ Repeat 3
 241 GGGAGAACTC TCCTCCCCAA TTAACCGTTT TTTTCTTCAT ATTTTCTACA CTACATATGC
 301 CTAAAATAAA TAATTGAGAG ATGAGTTAAG AGAAAGAAAA GGTAATGTAT AATGCTGGTT
 361 TTCAGGATGG TTGGTTTTAA GATCTAATTG TTATTATTCA CCGCCTAAAC GAACCTTTAA
 421 AATAAGCAT AACACAGCTC CTTAATTTCT CATTGGGCAT GGAGTTTTCT TGTTTGCTG
 481 GAGAGAAAGA AGACCTTTGA AATTTCAAAA CACTCTTTTG TGGCTAGTTT GAAAACTCGA
 541 ATCATCTCCA GGATCGACCG GAATTAGGGA ATAAATAAAC TATTTTTTCT CTCAATCTCA
                                                ──────▶ Repeat 2
 601 AAGACAATTT AAGTTTCCAA ACTAGCGATT AATCTTAACC AATGACTAGA CTTTGTGTTG
 661 GTTTTTTCTC TTACTGCTGG AGATGCTAAG GATTCTTCTT CCAAGAACGA CTAGAAACCG
     ──────▶ Repeat 1
 721 AATCGCTTTT TCCCTCGGCT AGTTTCGCAT GGCATCGTCC TTCCTGCCCA TGCGCGCACA
 781 ACCATCCATC CACTGACGAT GCGATGCCTA CCCACCACCT CGCGCAGCGT GATGCTAACG
                                 ─────────────▶ CTF/NF1 BINDING SITE
 841 CCACCACATG CACCACCAGT GGGGCAGCTG GGGACGCCGG GAGCAACCGG CAGCGCCCTA
                                                                  ──
 901 TAAATCTGCC GGCCCGGCCG TTGCATTGTC TGCGTCAGGG CCTCTTGATC ATCAGTCGCC
     ──▶ TATA BOX                                ◀── SDP
 961 AGAGGAGCTG TTGATCGAGG TGAGYGAGGT TGAAAAGCAG GCGGCGAACA AAGGCACCAT
     ─────────                                                    ◀──
     NcoI
1021 CGCCATGGAC GGC
     ─────────
       DO2460                                              FIG.4
```

MAIZE PROMOTER SEQUENCE FOR LEAF- AND STALK-PREFERRED GENE EXPRESSION

BACKGROUND OF THE INVENTION

1. Field of the Invention

This invention relates generally to mechanisms of gene expression in plants and more specifically to regulation of expression of genes in plants in a "tissue-preferred" manner. Regulation of expression is achieved using a transcriptional regulatory unit capable of driving expression of genes within certain tissues of a plant. Said transcriptional regulatory unit will ultimately be utilized for driving expression of genes that confer a selective advantage to a plant.

2. Description of the Related Art

Transcriptional control elements that drive "tissue-general" or "constitutive" gene expression in plants have been described. Examples include the promoters of the *Agrobacterium nopaline* synthase gene (Depicker, et al. 1982) and the maize ubiquitin gene (Christensen, et al. 1992). These promoters have been well characterized and utilized for driving gene expression in transgenic plants [e.g., CaMV 35S (Odell et al. 1985)]. There exists both an increasing interest in co-transforming plants with multiple plant transcription units and a realization of several potential problems associated with this technique. Concerns associated with the utilization of common regulatory sequences to drive expression of multiple genes include, but are not restricted to: a) recombination resulting from pairing along homologous regions, cross-overs and loss of the intervening region either prior to (in the case of a plasmid) or post-integration; b) hairpin loops caused by two copies of the sequence in opposite orientation adjacent to each other, again with possibilities of excision and loss of these regulatory regions; c) competition among different copies of the same promoter region for binding of promoter-specific transcription factors or other regulatory DNA-binding proteins; d) the relative strengths of expression of different promoters either within or between species, wherein one promoter may provide optimum levels of expression for one gene in a certain cell type or species, but may be either too strong or too weak for providing the required level of expression of a different gene in a certain cell type or species.

As part of our efforts to provide mechanisms for regulating the expression of genes that will ultimately be used for control of insect pests, primarily *Ostrinia nubilalis*, the European corn borer (ECB), we have been isolating and/or characterizing clones that exhibit intermediate to strong expression in the tissues that ECB primarily feeds on or tunnels through during its life cycle; these tissues include leaves, the leaf collar, the stalk rind and pith, and in the case of second generation ECB, pollen (Showers et al., 1989). While constitutive or "non-tissue-preferred" promoters have been demonstrated to be effective for this purpose such as the CAMV 35S promoter driving the *Bacillus thuringiensis* cryIA(b) gene provided effective ECB control in the field (Koziel et al., 1993), there are several advantages to utilizing promoters that function in a tissue-preferred manner. These include reduced resource drain on the plant in making a gene product constitutively, as well as localization or compartmentalization of gene expression in cases where the gene product must to be restricted to, or from, a certain tissue(s). Said gene products may include general cellular inhibitors such as RNases or other cytotoxins. As an example, Mariani, et al (Nature 347:737, 1990) engineered vectors that exhibited anther-specific gene expression of suc inhibitor genes for use in male sterility systems, since expression in regions other that the anther in a plant would be toxic. As an example of tissue-preferred expression, Koziel et al. (1993) utilized a combination of the maize PEP carboxylase promoter and a pollen promoter each driving cryIA (b) expression in separate constructs resulting in the generation of ECB-tolerant corn plants.

There is a need in the art for novel transcriptional regulatory elements which are capable of driving tissue-preferred gene expression in plants. It is considered important by those skilled in the art to continue to provide tissue-preferred transcription units capable of driving expression of genes that may confer a selective advantage to a plant.

SUMMARY OF THE INVENTION

This invention provides a transcriptional regulatory region of a gene that will be utilized to construct an expression vector for directing "tissue-preferred" gene expression in plants transformed with said expression vector such that said plants will retain a selective advantage over non-transformed plants. Said selective advantage may be conferred to said plants by expression of a gene encoding a polypeptide that confers resistance to insect or other pests. There exists a need in the art for transcriptional regulatory elements of plant genes which drive expression of said genes specifically or preferably within certain tissues of a plant. Such transcriptional units are defined to function in a "tissue-preferred" manner. The present invention relates to the isolation, characterization and utilization of a transcriptional regulatory region of a plant gene which is expressed in a tissue-preferred manner. The invention includes a method of isolation of plant tissue-preferred genes, isolated and purified DNA molecules comprising plant tissue-preferred genes or fragments thereof, methods of preparation of vectors comprising tissue-preferred transcriptional regulatory regions, and methods of generating transgenic plants comprising reporter or effector genes under the trasncriptional control of a tissue-preferred transcriptional regulatory region.

It is an object of the invention to provide a method for cloning of genes expressed in a tissue-preferred manner in plants.

It is another object of the invention to provide DNA molecules representing genes or fragments thereof which are expressed in a tissue-preferred manner.

It is yet another object of the invention to provide DNA molecules representing a transcriptional regulatory region of a gene which is expressed in a tissue-preferred manner.

It is also an object of the invention to provide a reporter construct useful for testing the ability of said transcriptional regulatory region to drive expression of a reporter gene in a tissue-preferred manner in vivo.

It is another object of the invention to provide a method useful for testing the ability of said transcriptional regulatory region to drive expression of a reporter gene in a "tissue-preferred manner in vivo.

It is a further object of the invention to provide DNA molecules that will be useful in the control of plant pests.

In one embodiment, a method for cloning plant genes that are expressed in a tissue-preferred manner is provided. The method comprises the construction of cDNA libraries using RNA of various tissues and screening said cDNA libraries with labelled mRNA from said various tissues. Clones are then isolated that represent mRNA species whose expression is upregulated in at least one tissue of said plant. In this manner, cDNA clones that represent mRNAs expressed in a tissue-preferred pattern are identified.

In another embodiment of the invention an isolated and purified subchromosomal DNA molecule is provided which contains a MS8-15 open reading frame (ORF) as shown in SEQ ID No:1 and FIG. 2.

In yet another embodiment, a transcriptional regulatory region of a said tissue-preferred gene is determined. A method comprising identification and characterization of a transcriptional regulatory region of said gene expressed in a tissue-preferred manner is provided.

In one embodiment of the invention an isolated and purified subchromosomal DNA molecule is provided comprising a transcriptional regulatory region of a MS8-15 gene is provided as shown in SEQ ID NO: 3 and FIG. 3.

In another embodiment of the invention a method is provided whereby said transcriptional regulatory region is isolated by PCR using synthetic oligonucleotides complementary to a region on said transcriptional regulatory region of said gene expressed in a tissue-preferred manner. In a preferred embodiment of the invention, said oligonucleotides each include at least one restriction enzyme excision site for convenient cloning into plant expression vectors.

In yet another embodiment of the invention, an isolated and purified subchromosomal DNA molecule is provided that contains a MS8-15 transcriptional regulatory region isolated by PCR using MS8-15 specific oligonucleotides. The sequence of said DNA molecule is shown in SEQ ID No: 5 and FIG. 4.

In another embodiment of the invention, a cloning vector comprising a MS8-15 transcriptional regulatory region is provided, as shown in FIG. 5.

In yet another embodiment of the invention, an expression vector in which expression of an assayable gene product is under the control of a MS8-15 transcriptional regulatory region is provided, as shown in FIG. 6.

In still another embodiment of the invention, transgenic plants useful in the identification of tissues in which a MS8-15 transcriptional regulatory region drives gene expression of an assayable product is provided. Said transgenic plants are useful to analyze the ability of a MS8-15 transcriptional regulatory region to drive tissue-preferred gene expression in vivo.

These and other objects of the invention will be apparent to those skilled in the art from the following detailed description of a preferred embodiment of the invention.

BRIEF DESCRIPTION OF THE DRAWINGS

FIG. 2. Sequence of the MS8-15 cDNA insert showing the MS8-15 open reading frames (ORF). The pMS8-15 cDNA clone was completely sequenced and the nucleotide and deduced amino acid sequence is disclosed in this figure. In addition to a complete MS8-15 ORF, two additional partial ORFs were identified within the pMS8-15 cDNA clone. The amino acid sequence of the complete ORF as well as that of the partial ORFs are shown. The partial ORF demonstrates homology to the GRP90 homologue as illustrated.

FIG. 3. Sequence of the MS8-15 5' upstream (promoter) region including a short portion of the coding sequence. A portion of the MS8-15 coding region from the pMS8-15 cDNA clone was utilized to probe a maize genomic library. A clone was isolated which contained nucleotide sequence of a 5' region of a MS8-15 gene and is shown in this figure.

FIG. 4. Sequence of PCR amplified MS8-15 promoter. A portion of the 5' upstream region of a MS8-15 gene (the MS8-15 promoter) was amplified by PCR using oligonucleotides complementary to the sequence of a MS8-15 gene. Said oligonucleotides each include at least one restriction enzyme site for cloning of the PCR-amplified DNA into cloning and expression vectors.

Figure 1:
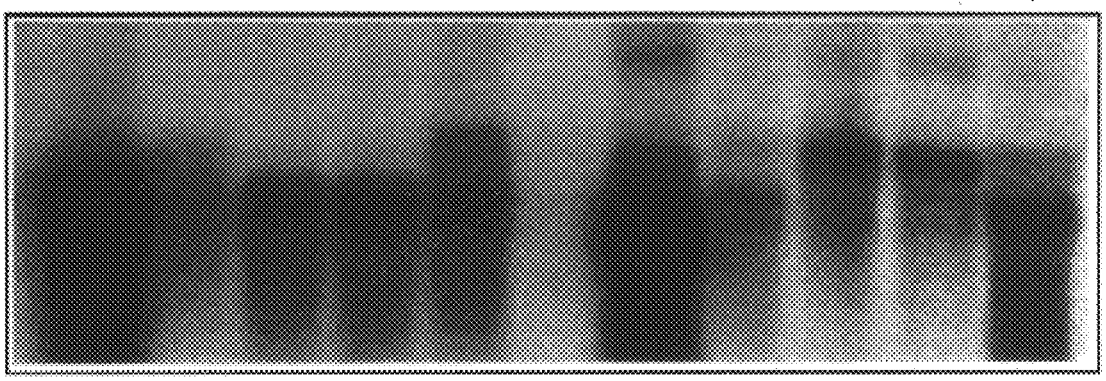
FIG. 1. Northern blot of total RNA from different maize tissues probed with an internal fragment of the pMS8-15 cDNA clone. The pMS8-15 cDNA clone was isolated using differential library screening of gene expression in specific tissues of maize and cloning of cDNAs which represent genes exhibiting a tissue-preferred pattern of expression. The northern blot in this figure demonstrates the tissue-preferred pattern of expression of one such clone, pMS8-15.

Table I. pMS8-15 Promoter GUS Expression in T1 Maize Tissues. Transgenic maize plants which have incorporated into their genome the pPHI5933 expression vector were harvested and various tissues assayed for uidA (GUS) expression. The data indicate a "green-tissue preferred" pattern of expression driven by the MS8-15 promoter.

DETAILED DESCRIPTION OF THE INVENTION

Within this application, a transcriptional regulatory region is defined as any element involved in regulating transcription of a gene, including but not limited to promoters, enhancers and repressors.

A DNA fragment is defined as a segment of a single- or double-stranded DNA derived from any source.

A DNA construct is defined as a plasmid, virus, autonomously replicating sequence, phage or linear segment of a single- or double-stranded DNA or RNA derived from any source.

A gene product that confers a selective advantage to a plant is defined as any gene product which, upon expression in said plant, confers increased growth rate, yield of product or resistance to threats to said plant's ability to thrive including but not limited to pathogens, pests, adverse weather conditions, and herbicides relative to plants that do not express said gene product.

The term operably linked refers to the combination of a first nucleic acid fragment representing a transcriptional control region having activity in a cell joined to a second nucleic acid fragment encoding a reporter or effector gene such that expression of said reporter or effector gene is influenced by the presence of said transcriptional control region.

A gene expressed in a tissue-preferred manner is that which demonstrates a greater amount of expression in one tissue as opposed to one or more second tissues in a plant specimen.

A gene defined as green-tissue preferred is a gene that is expressed at a higher level in plant organs at least partially comprised of cells exhibiting chlorophyll synthesis.

A regenerable culture is defined as a cell or tissue culture that can be manipulated so as to allow regeneration of plants.

Transgenic plant defines a plant in which a gene has been added to the germline of said plant.

A mature plant is defined as a plant in which normal development of all vegetative and reproductive organs has occurred.

A gene product useful in controlling pests defines any gene that functions to inhibit the growth, migration, existence or behavior of any pest that may threaten the normal life cycle of one or more organisms.

An assayable product includes any product encoded by a gene that is detectable using an assay. Furthermore, the detection and quantitation of said assayable product is anticipated to be directly proportional to the level of expression of said gene.

A reporter construct is defined as a subchromosomal and purified DNA molecule comprising a gene encoding an assayable product.

An expression vector is defined as a subchromosomal and purified DNA molecule comprising a transcriptional regulatory region driving expression of a gene.

To isolate transcriptional regulatory regions useful for driving tissue-preferred expression of effector genes in plants, it is necessary to identify genes that demonstrate a tissue-preferred pattern of expression in plants. One method of identification is PCR-based differential display analysis (Liang, et al. Science 257:967). This methodology involves the use of random oligonucleotide primers, PCR-amplification of RT-cDNA and comparison of patterns of expression between at least two samples. Said samples may include but are not limited to different types of cells or tissues, cells or tissues in various stages of development, or cells or tissues that have been exposed to various chemicals or conditions and may result in a change in gene expression in said cells or tissues. Non-identical DNA banding patterns of DNA amplified from said samples indicate a difference in gene expression between samples. DNA corresponding to the bands which exhibit said non-identical DNA banding patterns are cloned and utilized to identify the genes to which the DNA bands correspond. An alternative method involves the use of subtractive hybridization (Lee, et al. Proc. Natl. Acad. Sci. 88:2825). This methodology involves the hybridization of cDNA (antisense) of sample A and biotinylated-RNA of sample B. Biotinylated-RNA molecules of sample B representing genes expressed in both samples will hybridize to the complementary cDNA molecules of sample A and will be destroyed by subsequent enzymatic treatment. Following purification of the remaining biotinylated RNA molecules of sample B, a cDNA library is constructed using said remaining biotinylated RNA of sample B. The clones of said cDNA library represent genes that are preferentially expressed in sample B. A further method is by screening of a cDNA library of a first sample using labelled RNA representing a second sample. Clones of said cDNA library of said first sample that do not hybridize to said labelled RNA of said second sample represent mRNA species that are not expressed in said second sample. Alternatively, several libraries may be individually screened using labelled RNA from several separate samples. If said samples are different tissues of a plant, altered patterns of hybridization in one sample as compared to another sample indicates a tissue-preferred pattern of gene expression. cDNA clones isolated in the above-described manner will represent mRNA species that are preferentially expressed in a sample or a group of samples.

It is then necessary to confirm that a cDNA isolated by any of the above-described techniques or any other technique resulting in the isolation of potentially tissue-preferred plant genes is expressed in a tissue-preferred manner. RT-PCR is a method by which mRNA represented by a potentially tissue-preferred cDNA is amplified from a cell or tissue of interest (Berchtold, et al. Nuc. Acids Res. 17:453). Amplification of said mRNA from several different tissues allows for a comparison to be made and the relative level of expression of mRNA of said potentially tissue-preferred plant gene to be determined. Another method which may be utilized to determine the level of gene expression in a plant cell or plant tissue is RNase protection assays (Melton, et al. Nuc. Acids Res. 12:7035). RNA from the samples to be compared is hybridized to a labelled antisense RNA probe generated from a cDNA representing a mRNA of a plant gene potentially expressed in a tissue-specific manner. This is followed by the addition of RNase. All RNA which has hybridized to said labelled antisense RNA probe is protected from degradation (termed protected transcripts) by the RNase while mRNA that has not hybridized to said antisense labelled RNA probe is degraded. The products are then separated by gel electrophoresis and protected transcripts detected using detection methods including but not limited to autoradiography. The relative intensity of the band corresponding to said protected transcripts is proportional to the level of expression of that protected RNA species in each tissue. An additional method with which tissue-preferred expression may be determined is by northern blot analysis (Alwine, et al. Proc. Natl. Acad. Sci. 74:5350). RNA from a sample of interest is isolated and separated by gel electrophoresis. The separated RNA species are then transferred to a membrane and probed with a labeled nucleic acid probe that is complementary to RNA representing a gene of interest. Hybridization is detected using a detection method including but not limited to autoradiography. The intensity of the band corresponding to RNA representing a gene of interest is determined and is proportional to the level of gene expression in each sample. A tissue-preferred gene is identified by increased hybridization in one tissue as compared to a second tissue of a plant.

It is then desirable to isolate the transcriptional regulatory region responsible for driving expression of said gene of interest in a tissue-preferred manner. This region may be isolated by several methods including but not limited to amplification of a region of DNA comprising said transcriptional regulatory region. Said DNA is amplified from genomic DNA maintained as a genomic DNA library in a cloning vector including but not limited to phage, plasmids, cosmids, yeast artificial chromosomes (YAC) or any other vector capable of harboring fragments of chromosomal DNA. Said transcriptional regulatory region of said gene expressed in a tissue-preferred manner may be isolated by amplification of the genomic sequences encoding the cDNA sequence. Two oligonucleotide primers, the first comprising sequence complementary to a region within the nucleotide sequence of said cloning vector and the second comprising sequence complementary to a 5' region of said cDNA encoding a gene expressed in a tissue-preferred manner, are utilized in a PCR reaction. The template for said PCR reaction comprises a portion of said genomic DNA library. Amplification products may include but are not limited to DNA comprising a 5' transcriptional regulatory region of said gene of interest, the remaining 3' sequence of said cDNA including a 3' untranslated region, or fragments thereof. DNA sequencing of each amplified product results in identification of those clones comprising a potential transcriptional regulatory region (Frohman, et al. Proc. Natl. Acad. Sci. 85:8998). A further method for isolation of the transcriptional region of a gene expressed in a tissue-preferred manner includes utilization of the cDNA or fragment thereof encoding the gene of interest as a cDNA probe to screen said genomic DNA library by hybridization. Clones which demonstrate hybridization to said cDNA probe are isolated and characterized by restriction enzyme mapping and nucleotide sequence analysis.

To construct expression vectors useful for testing the transcriptional regulatory region of a gene expressed in a tissue-preferred manner, the elements responsible for said ability to drive tissue-preferred gene expression are determined and isolated. Said elements are then inserted into the transcriptional control region of an expression vector such that said transcriptional control region is linked in cis to a gene encoding an assayable product. Said assayable product may include but is not limited to beta-glucuronidase (GUS™), luciferase, beta-galactosidase, green fluorescent protein (GFP) or chloramphenicol acetyltransferase (CAT). Said elements responsible for tissue-preferred gene expression are isolated using methods including but not limited to the following procedures. Nucleotide sequence and restriction enzyme maps of said genomic clones that demonstrate hybridization to said cDNA probe are determined. Using restriction enzyme digestion and subcloning methods well known to those skilled in the art, expression vectors are constructed comprising various regions of said genomic clone linked in cis to a gene encoding said assayable product to generate an expression vector in which expression of an assayable product is driven by said various regions of said genomic clone. A further method includes the utilization of an oligonucleotide comprising nucleotide sequence complementary to the 5' region of said transcriptional control region of said gene expressed in a tissue-preferred manner and an oligonucleotide comprising nucleotide sequence complementary to a 3' transcriptional control region of said gene expressed in a tissue-preferred manner are synthesized. Preferably, each oligonucleotide further comprises nucleotide sequence corresponding to restriction enzyme sites compatible for cloning into an expression vector encoding an assayable product. Following amplification of DNA comprising the transcriptional control region, cloning of said region into said expression vector is accomplished using techniques well known in the art. Use of the above-described methodologies results in the construction of expression vectors comprising separate potential transcriptional control regions linked in cis to a gene encoding an assayable gene product.

To confirm that said transcriptional control region functions in a tissue-preferred manner in plant tissues, said expression vector comprising a transcriptional control region of a gene expressed in a tissue-preferred manner in plants linked in cis to an assayable product is transfected into plant cells or tissues. The method utilized for transfection of various types of plant cells or plant tissues may include but is not limited to particle bombardment, liposome-mediated transfection, calcium phosphate-mediated transfection, bacterial- or viral-mediated gene transfer, electroporation, or Argobacterium-mediated transformation. Said various cells or tissues may be transfected in vitro after excision from said plant. Following a defined period of time after transfection of said construct into said tissues, the tissues are harvested and an assay capable of detecting said assayable product is performed. The amount of assayable product detected in said cells or tissues is proportional to the ability of said transcriptional control region to function in that cell or tissue. In this manner, the ability of said transcriptional regulatory region to drive tissue-preferred gene expression is determined. Alternatively, said cells or tissues may be utilized to generate a transgenic plant. Said transgenic plants have at least one copy of said expression vector comprising said transcriptional control region linked in cis to a gene encoding an assayable product incorporated into the genome of the plant. Said copy is therefore present in each cell and tissue of said transgenic plant. Harvest of said tissues is followed by assay of said tissues for expression of said assayable product. The amount of said assayable product in each of said tissues is determined and is proportional to the level of expression of said gene encoding said assayable product in each of said tissues. In this manner, the ability of the transcriptional control region of said cDNA to drive tissue-preferred gene expression is determined.

The ability of said transcriptional control region to drive tissue-prefered expression of genes may also be tested by the generation of transgenic plants in which the transgene comprises a tissue-preferred transcriptional control region driving expression of an effector gene that confers a selective advantage to those plants comprising said transgene. Said transgenic plants are allowed to mature and are then challenged by a pest which may exhibit a response to expression of said effector gene in a plant. Preferably, the pest is selected from a group of pests which are present for at least a portion of their lifespan in a tissue in which said transcriptional control region drives gene expression. The behavior of said pest is demonstrated to be altered in those tissues in which the effector gene is expressed. The change in said behavior of said pest includes but is not limited to altered growth characteristics, inability to thrive, or death. An example of one such effector gene is the cry IA(b) gene that has been demonstrated to function in the generation of plants resistant to the European Corn Borer (Koziel, 1993).

Said transcriptional control region may also be utilized to drive expression of genes involved in other aspects of plant physiology including but not limited to resistance to pests other than insects, resistance to herbicides, growth of the plant, resistance of fruits or vegetables to spoiling, or resistance to adverse weather conditions. Said pests other than insects may also include but are not limited to bacteria, parasites, fungi, viral agents, viroids including but not limited to the fungi, fusarium and fumonsin, or the virus known as the Tobacco Mosaic Virus. The growth characteristics of a plant include but are not limited to those that result in the production of increased amounts of fruit, increased amounts of seed, growth at either a faster or a slower rate, or growth in a season other than that considered ordinary for said plant. Adverse weather conditions to which the plant may become resistant include but are not limited to temperatures above or below that which the plant is not ordinarily able to survive, flooding, and drought.

The following examples illustrate particular embodiments of the present invention and are not limiting of the specification and claims in any way.

EXAMPLE 1

Isolation and Characterization of the cDNA Clone MS8-15

To isolate a tissue-preferred gene from maize, four cDNA libraries were constructed and utilized for differential screening to identify cDNA clones which exhibit tissue-specific patterns of expression. RNA was isolated from 1 week old roots, 1 week and 8 week old stalks and 4 week old wounded leaf tissue of *Zea mays* L. (cv.B73) by standard methods. Briefly, tissues were ground to a powder in liquid nitrogen, resuspended in buffer (100 mM LiCl, 100 mM Tris-HCl, pH 8.0, 100 mM EDTA, 1% SDS), extracted with phenol:chloroform:isoamyl alcohol (25:24:1), and the supernatant was incubated overnight with 2 M (final concentration) LiCl. The RNA was ethanol precipitated, washed and resuspended in sterile RNAase-free water. Poly (A)+ mRNA was isolated using oligo(dT) cellulose chromatography (Aviv and Leder, 1972) and utilized to construct cDNA libraries in the LambdaGEM4 vector (Promega, Madison, Wis.) using a cDNA synthesis kit (Boehringer Manheim, Indianapolis, Ind.). Briefly, a poly(dT) primer containing extra bases at the 5' end which included the recognition sequence for XbaI was annealed to the poly(A) tail of the mRNA and cDNA was synthesized using reverse transcriptase. Second strand synthesis was followed by addition of an EcoRI linker to the 5' end of the double stranded cDNA and subsequent directional cloning into the LambdaGEM4 vector.

Approximately $1 \times 10^6$ plaques from each library were plated and differentially screened using labeled poly(A) mRNA from the other tissues as probes (Negruk et al., J. Virol. Meth. 1:229, 1980). In the process of selecting for plaques exhibiting tissue-preferred expression patterns, some plaques were identified which, following secondary and tertiary screening, hybridized strongly to leaf and stalk tissue probes. One such clone, termed pMS8-15, was selected for further analysis.

It was necessary to confirm that the pMS8-15 cDNA clone represented an mRNA species which was expressed in a tissue-preferred manner in a plant. RNA isolated from various maize tissues was probed with the pMS8-15 probe to assay the tissue-preferred expression patterns of the MS8-15 mRNA. Two grams of tissue from a number of maize (cv.B73) tissues including 11 week old leaf blade, leaf whorl, leaf collar, stalk rind, stalk pith, stalk node, and seedling roots were frozen in liquid nitrogen and total RNA isolated using TRI REAGENT (Molecular Research Center, Inc., Cincinnati, Ohio) as indicated by the supplier. Eight grams of maize kernels at 4, 14 and 27 days post pollination were frozen in liquid nitrogen and total RNA was isolated as described by Wessler (1994). The RNA was resuspended in formamide and concentrations adjusted to 5 ug/ul. Approximately 10 ug of each RNA was run on a 1.4% formaldehyde denaturing gel. Samples were heated to 65° C. prior to loading and were run in a formaldehyde-based running buffer. The gel was then washed for 30 minutes in DEPC-treated double-distilled water and then photographed. Gels were transferred to Magna Charge membrane (MSI, Westborough, Mass.) by capillary blotting overnight. Membranes were then baked at 80° C. for one hour and subjected to UV cross-linking using a Stratalinker (Stratagene, La Jolla, Calif.). Membranes were prehybridized for two hours in 50% formamide, 5× Denhardt's, 5× SSPE and 0.1% SDS containing 200 ug/ml heat-denatured herring sperm DNA and 50 ug/ml tRNA. DNA probes were labeled with $^{32}$P-dCTP using a random primed labeling kit (Boehringer Manheim, Indianapolis, Ind.). Probe DNA was denatured at 95° C. for 10 minutes, added to the membranes in fresh prehybridization solution, and allowed to hybridize overnight at 42° C. Blots were washed in 2× SSC, 0.1% SDS twice for 20 minutes at 65° C. followed by two washes in 0.1× SSC, 0.1% SDS twice for 20 minutes at 65° C. Membranes were rinsed briefly in water, then wrapped in cellophane and subjected to autoradiography at −80° C. using Kodak XAR5 film and two intensifying screens.

Northern blot analysis in which total RNA from a broad range of maize tissues was hybridized with the pMS8-15 cDNA clone insert revealed differential hybridization in a number of the tissues examined (FIG. 1). Hybridizing bands are present in most tissues, with the strongest signals present in leaf and stalk node RNA. The hybridizing band corresponds to an mRNA of approximately 1.1 to 1.2 kb in size. A second mRNA (approx. 1.4 kb) appears to be expressed in maturing seed and to a lesser extent in whorl and pith tissue. This observation agrees with Southern blot results (not shown) which indicate that there are likely two genes showing significant homology to the cDNA insert (data not shown). These results suggested that the promoter for the pMS8-15 clone might be useful in driving expression of genes in a leaf/stalk-preferred manner, and thus may be suitable for driving expression of genes such as those useful for control of the European corn borer.

In an attempt to identify the MS8-15 gene, the 1.207 kb pMS8-15 cDNA insert was completely sequenced in both directions by the dideoxy chain termination method (Sanger et al., 1977) using multiple primers along the length of the cDNA clone (FIG. 2; SEQ ID NO: 1). Complete sequencing of the 1.207 kb pMS8-15 cDNA clone and subsequent comparison of the internal uninterrupted ORF to sequences in the GenEMBL and Swissprot databases using the BLAST protocol revealed no significant sequence similarity to any known gene sequences. Analysis did reveal that the 8–15 insert was in fact a fusion of three open reading frames. The first two hundred bases (approximate) showed 87% homology at the nucleotide level and greater than 90% at the amino acid level to a *Hordeum vulgare* (Barley) cDNA coding for a GRP90 homologue. The last 50 bases also showed 100% homology to a rat alcohol dehydrogenase cDNA. While it appears that these two additional partial cDNAs were incorporated into the pMS8-15 clone during the cloning process, all characterization was completed using the sequences corresponding to the pMS8-15 ORF. The complete MS8-15 internal open reading frame indicated some homology to several ESTs from rice, one from maize and one from Arabidopsis, these having no defined function to date. It cannot be determined if the observed sequence identity would reflect functional similarity without full characterization of the various gene products. Emphasis for promoter isolation concentrated on the internal unidentified ORF since said ORF represented the largest full-length ORF and comprised the region of DNA utilized as a probe in northern blot analysis. A genomic clone corresponding to MS8-15 was isolated, sequenced and characterized.

To determine the transcriptional regulatory region of the MS8-15 gene, the pMS8-15 cDNA was utilized to isolate genomic clones representing the MS8-15 gene. A 1.25 kb EcoRI/XbaI fragment was isolated from the pMS8-15 cDNA clone and labeled with digoxigenin-11-dUTP by the random primer method using the protocol exactly as outlined in the Genius™ system users guide (Boehringer Manheim, Indianapolis, Ind.). Approximately $1 \times 10^6$ plaques from a maize genomic library constructed in lambda DASH (Stratagene, La Jolla, Calif.) were screened using the combined labeled fragments as a probe, and two positive clones were recovered. DNA from each of the two genomic clones was isolated and digested with a number of restriction enzymes (several of which cut internally in the cDNA), separated on a 1% agarose gel, transferred onto membranes and hybridized with the digoxigenin labeled 1.25 kb EcoRI/XbaI fragment. The two clones (15-30 and 34-1) are identical. A 4.7 kb EcoRI and a 6.0 kb SalI fragment from each genomic clone was isolated and subcloned. The EcoRI cloned fragment was further subjected to multiple single and double digests which allowed generation of a partial restriction map, from which two fragments, a 1.7 kb EcoRI/NotI and a 3.0 kb EcoRI/NotI fragment were subcloned into the corresponding sites of pBlueScriptII (SK+) (Stratagene, La Jolla, Calif.). The genomic insert fragments were partially sequenced in order to determine the orientation of the cloned fragments with respect to the cDNA probe since the cDNA was thought to span both fragments. The 1.7 kb EcoRI/NotI fragment was sequenced in its entirety and was found to contain sequences corresponding to the 5' upstream (promoter) region of the pMS8-15 clone.

DNA sequencing of the genomic clone showed sequence identity over the length of the coding portion of the internal ORF of the MS8-15 cDNA clone. Analysis of the region 5' of the observed putative ATG translation initiation site in this genomic clone reveals an obvious TATAAA sequence at −126 from the start of translation (FIG. 3). Additionally, the cDNA and genomic sequences match exactly over 88 nucleotides directly upstream of the translation start site, to the point where the partial upstream ORF ends (compare to FIG. 2). This point of divergence is also 32 nucleotides downstream of the putative TATAAA sequence. In addition, a potential mRNA cap site exists within the proximal 5' upstream region (indicated in FIG. 3). A sequence showing similarity to a transcription factor binding site is present at about 220 nucleotides upstream of the ATG. This site shows homology to both the CAAT box binding factor site and the NF1 binding site in some mammalian promoters such as the albumin promoter (Cell 48: 79). The GC content falls to 44% in the first 1000 base pairs of the promoter. There is also a significant number of poly(T) stretches in the distal 5' region of the promoter. In addition, there are polypyrimidine repeats consisting of five to six T residues followed by CTC (TTTTTTCTC) at −358, −437 and −804 respectively. Deletion or mutation analysis could help determine the functionality associated with these repeated sequences.

EXAMPLE 2

Construction of MS8-15 Promoter Expression Vectors

Figure 5:
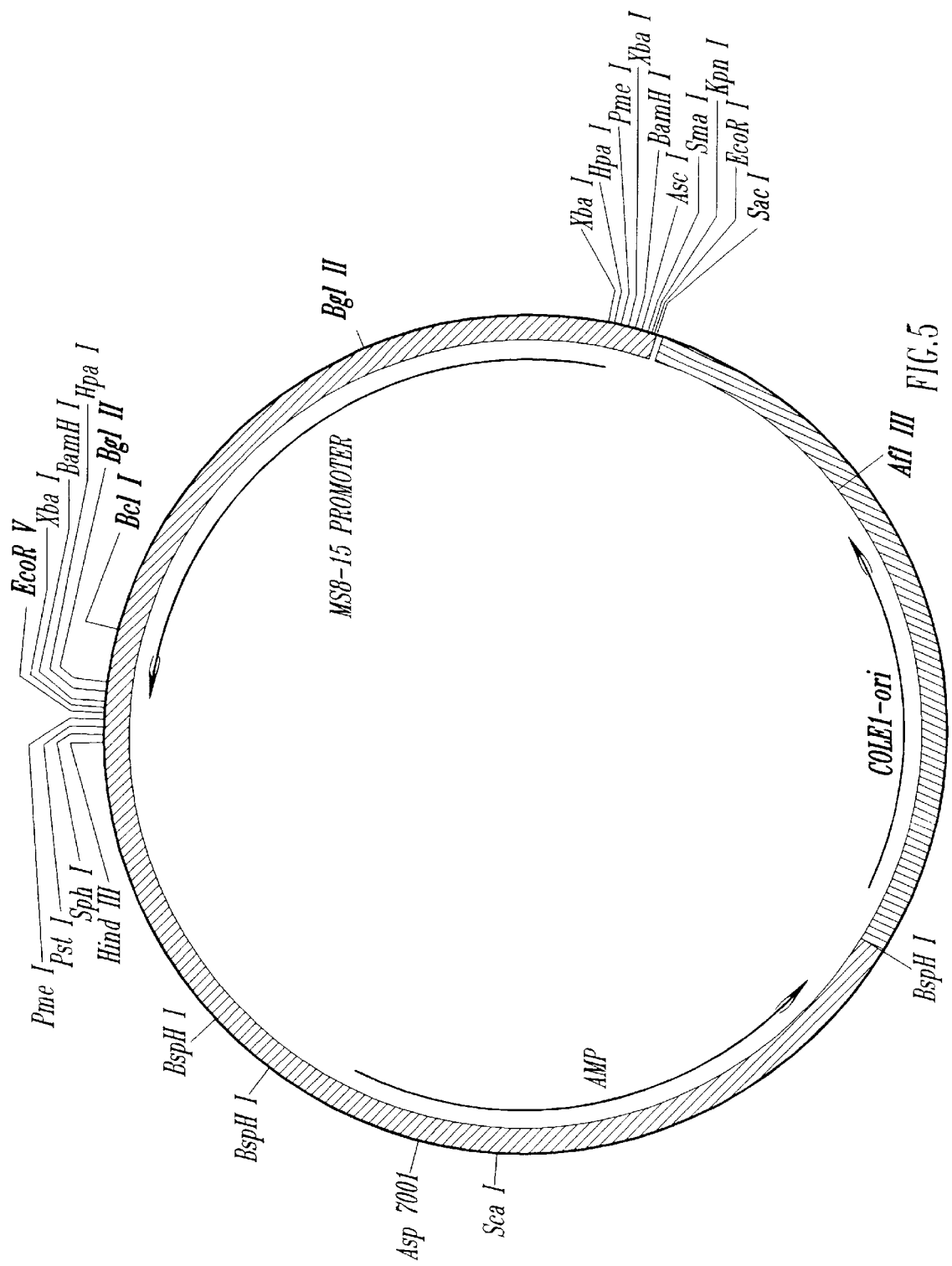
FIG. 5. Map of the Vector pPHI8245 which contains the MS8-15 PROMOTER (shown in FIG. 4) cloned into pBlueScriptII (SK+).
Figure 6:
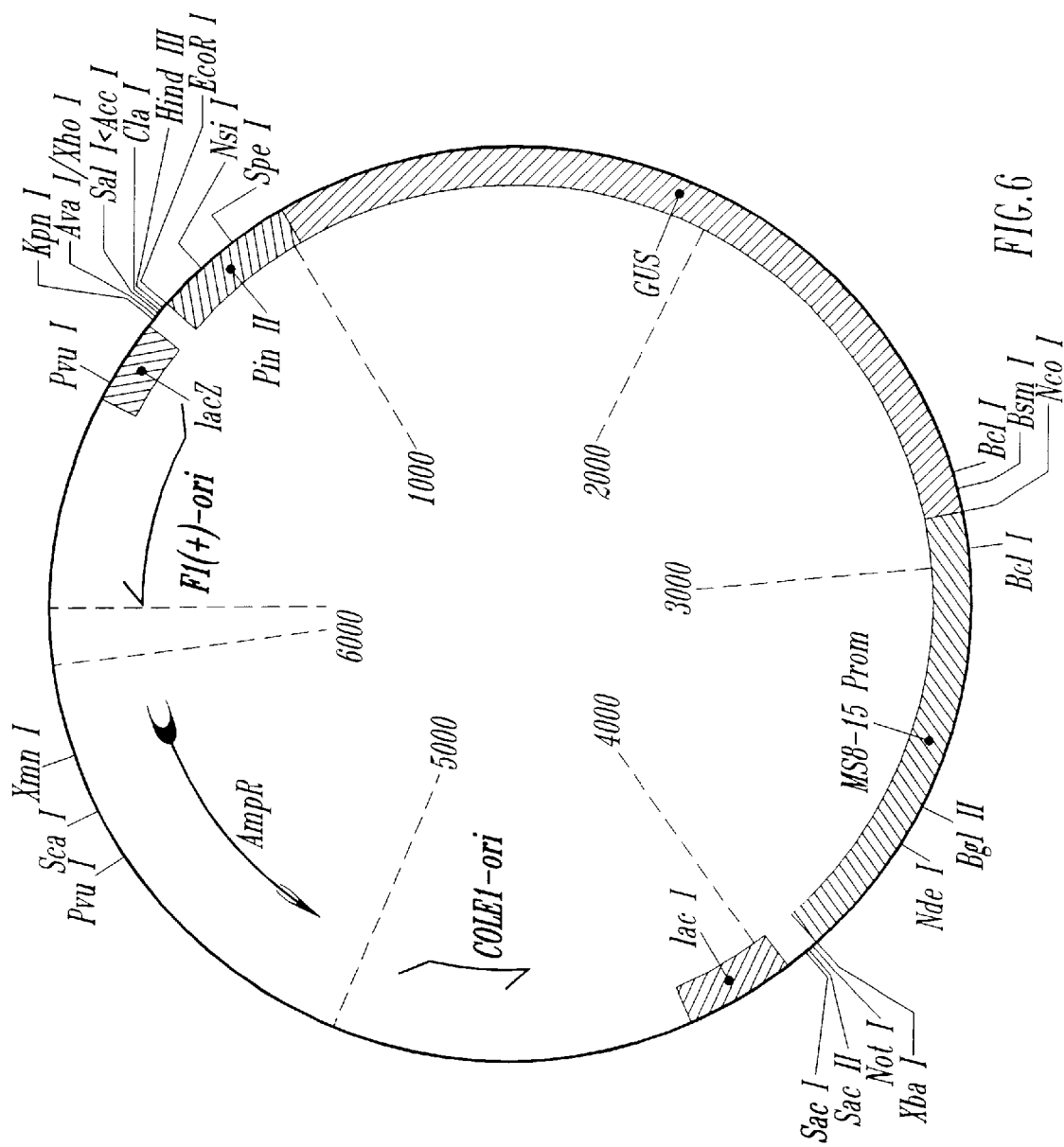
FIG. 6. Map of pPHI5933 containing the MS8-15 promoter driving expression of the GUS reporter gene, and including the PinII 3' terminator sequence. A reporter gene, uidA (GUS) was cloned in a downstream cis orientation relative to the MS8-15 promoter to generate the expression vector pPH15933. The uidA gene encode s an assayable gene product.
Figure 7:
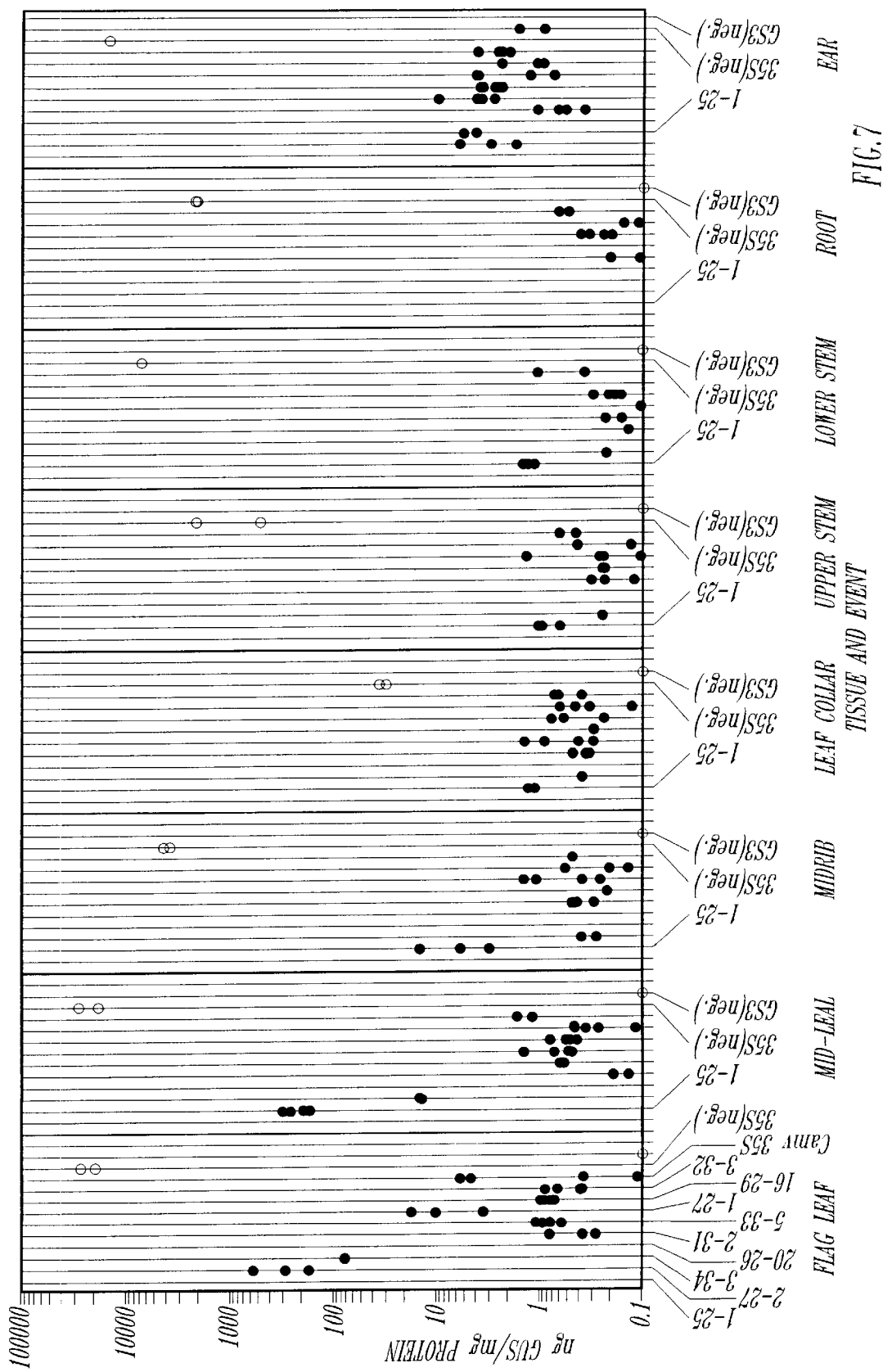

As a result of our previous success using PCR to amplify putative promoter sequences of plant genes for testing functionality in transgenic plants (Baszczynski et al., unpublished), we adopted this approach to design a pair of oligonucleotide primers (see Materials and Methods) that would simultaneously allow amplification of the target promoter sequence and provide convenient restriction sites at the ends of this promoter for cloning into plant transformation vectors (Boutilier, et al. Plant Mol. Biol. 26:1711–1723, 1994). The MS8-15 promoter is defined as the 1012 bp of the MS8-15 gene which lies adjacent to and upstream of the deduced AUG translation initiation codon. It is also understood that shorter regions of said MS8-15 promoter, as could be generated and studied using deletion analysis techniques, may provide the sufficient tissue-preferred levels of gene expression The nucleotide sequence of the final PCR amplified product is shown in FIG. 4 and SEQ ID NO: 5, which, following appropriate digestion was used to generate two vectors as shown in FIGS. 5 and 6. pPHI8245 (FIG. 5) simply contains the MS8-15 promoter in pBlueScriptII (SK+) (Stratagene, La Jolla, Calif.) for use in subsequent cloning. pPHI5933 (FIG. 6) is a plant transformation vector comprising the MS8-15 promoter and the uidA (GUS) gene to test the functionality of the promoter in transgenic plants.

Two oligonucleotides were synthesized and used to amplify, by PCR, 1012 bp of the 5' region directly upstream of the deduced AUG translation initiation codon as determined by sequence alignment to the cDNA sequence and presence of promoter-associated sequences such as the TATA box. The oligonucleotides included additional 5' sequence to add restriction sites to aid in cloning the final PCR amplified product. Oligonucleotide D02461 (5'-CCGGTTAACTCTAGAGGGTAGCAGAG-CATAGTCAGTG; SEQ ID NO: 6), complementary to the 5' end of the putative promoter, included introduced HpaI and XbaI sites. Oligonucleotide D02460 (5'GCCGTCCATGGCGATGGTGCC; SEQ ID NO: 7), complementary to the antisense strand at the 3' end of the putative promoter, contained sequences designed to introduce by mutation an NcoI site at the ATG start codon. The NcoI site was generated in order to create translational fusions with other genes of interest.

Ten ng of template DNA of the 1.7 kb EcoRI/NotI fragment was combined on ice with 50 ng of each of primers D2460 and D02461 in a 50 ul reaction mix containing (final concentrations) 50 mM KCl, 10 mM Tris-HCl (pH 8.3), 2 mM MgCl$_2$ 0.001% gelatin, 200 uM of each of dATP, dCTP, dGTP and dTTP, and 5U of AmpliTaq polymerase (Perkin-Elmer/Cetus, Norwalk, Conn.). The reaction tube was heated at 94° C. for 2 minutes to denature template DNA and then subjected to 30 cycles of 1 minute at 94° C., 2 minutes at 63° C. and 2.5 minutes at 72° C., followed by a 10 minute final incubation at 72° C. using a Perkin Elmer Thermal Cycler 480. A sample of the PCR amplified promoter was digested with XbaI and NcoI, and cloned into the corresponding sites of pBlueScriptII (SK+) (Stratagene, La Jolla, Calif.) to produce vector pPH18245. A second sample of the PCR amplified promoter was digested with XbaI and NcoI, combined with a 2188 bp NcoI/EcoRI fragment containing the uidA (GUS) gene fused to the 3' non-coding region (terminator) from a potato proteinase inhibitor (PinII) gene, and cloned together into the XbaI/EcoRI sites of pBlueScriptII (SK+) to yield pPHI5933.

EXAMPLE 3

Analyses of MS8-15 Promoter Expression in Transgenic Maize

It was necessary to demonstrate that said MS8-15 promoter region would drive gene expression in a tissue-preferred manner in vivo. A model system was generated which allowed for testing of the MS8-15 promoter expression vector in maize. DNA of the plasmid pPHI5933 or of an insert region from pPHI5933 that excluded the pBlueScriptII (SK+) vector sequences was used to stably transform regenerable maize Hi-II callus cultures via the particle gun bombardment method. The method utilized for transfection of various types of plant cells or plant tissues may also include but is not limited to liposome-mediated transfection, calcium phosphate-mediated transfection, bacterial- or viral-mediated gene transfer, electroporation, or Agrobacterium-mediated transformation. A second vector, either pPHI5675 carrying the bar selectable marker gene behind a CaMV 35S promoter or pPHI5702 carrying the PAT selectable marker gene behind the CaMV 35S promoter, was co-bombarded and used to select for transformed events. Vector or inserts in which the uidA gene was under the control of a CaMV 35S promoter (pPHI264) were bombarded in parallel experiments for comparison of promoter activities. Immediately after bombardment, Hi-II culture events were incubated at 27° C. in the dark for 6 days followed by transfer to selective media containing 3 mg/L bialophos (Meiji Seika, Japan). About 6 weeks later putative transformed colonies were transferred onto regeneration media. After several weeks, developing embryos or scutellar structures were transferred and cultured separately in the light and transgenic maize plantlets were recovered.

Following regeneration of plantlets in test tubes from HiII callus cultures, five seedlings of each event were stained in McCabe's stain to select positive events to take to the greenhouse. For all events that exhibited some GUS staining in seedlings, sibling plants were potted and grown to maturity in the greenhouse. Following regeneration of up to 15 transgenic (T0) plants per event, ears were pollinated with HG11 pollen and allowed to mature in the greenhouse. At 5–9 days after pollination (dap), samples from each of the flag leaf, the leaf below the ear node (mid-leaf), midrib, leaf collar, upper stem, lower stem, root and ear section were collected and processed. For visual analysis of promoter activity, the plant tissues from transgenics were incubated for 18–36 hours in McCabe's stain. Transgenics with equivalent 35S-GUS constructs and negative control transgenics were assayed also for comparison. Additionally, small segments of maize tissues were frozen in liquid nitrogen, and used for quantitative GUS assays via the GUS-Light™ chemiluminescent detection system using conditions and solutions specified by the manufacturer (Tropix, Inc., Bedford, Mass.). Total soluble protein concentrations were measured using the BCA protein assay (Pierce, Rockford, Ill.) and BSA as a standard. Two ul of extract from two samples of tissue collected from two plants of each event were used for each determination. GUS expression was expressed as ng GUS/mg protein (ppm) and plotted for all transgenic events analyzed. T1 seed collected from sibling plants allowed to complete development were grown to maturity in the greenhouse, and samples were collected and analyzed again as for the T0 plants.

In all positive seedling events stained with McCabe's stain and observed visually, prominent GUS expression was observed primarily along the vascular bundles in the basal portion of the leaf and sheath, with some expression also in other regions of the leaf blade. Roots exhibited no expression in any of the seedlings stained. Tissues from the mature transgenic plants generally showed low levels of GUS staining. A positive 35S-GUS control event stained intensely in most tissues and stages examined. The GUS-Light™ chemiluminescence detection system and the BCA protein assay were used subsequently to quantitate the amount of GUS protein expression in the different tissues. Table 1 summarizes GUS expression data in T1 plants for each of the tissues examined for several events recovered from transformation with pPHI5933, or for two events recovered with the CaMV 35S promoter-GUS construct (pPHI264), one which was positive and one negative for GUS expression. Each point represents one sample analyzed for GUS expression. There is clearly variation in expression levels between events, as is typically observed in plant transformation experiments utilizing methods such as particle gun bombardment. This variation may be attributable to multiple or varying integration sites (position effects), DNA rearrangement during integration, or event-specific transgene quieting or instability. The data reveals that while the MS8-15 promoter is a weaker promoter than 35S, MS8-15 exhibits preferred expression in leaf tissues in those events showing expression. Events 1–25 and 2–27 exhibited the strongest expression among all MS8-15 events in both the T0 (not shown) and T1 generations (Table I). Although expression is not restricted exclusively to leaves, this tissue preference offers utility where it is desirable not to have strong expression of transgenes in all plant tissues. Additionally, higher levels of expression, such as with the CaMV 35S promoter or the maize ubiquitin promoter (Christensen et al., 1992), may not be required or desired in certain applications, as with expression of highly efficacious [e.g., cryIA(b)] or potentially cytotoxic (e.g., RNAase) gene products. This promoter thus provides a suitable alternative for expressing genes in plants.

While a preferred form of the invention has been shown in the drawings and described, since variations in the preferred form will be apparent to those skilled in the art, the invention should not be construed as limited to the specific form shown and described, but instead is as set forth in the claims.

What is claimed is:

1. An isolated DNA molecule comprising a plant transcriptional regulatory region of a MS8-15 gene as shown in SEQ ID NO: 3 or SEQ ID NO: 5.

2. An expression vector comprising a DNA molecule of claim 1 that further comprises a reporter gene encoding an assayable product, wherein expression of the reporter gene is driven by the transcriptional regulatory region of claim 1.

3. An expression vector comprising a DNA molecule of claim 1 that further comprises a gene that confers a selective advantage, wherein expression of the gene is driven by the transcriptional regulatory region of claim 1.

4. An expression vector comprising a DNA molecule of claim 2 or 3 wherein said transcriptional regulatory region comprises the nucleotide sequence as shown in SEQ ID NO: 3 or in SEQ ID NO: 5.

5. A method of generating a transgenic plant comprising: transformation of regenerable cultures or tissue segments with a transgene comprising a reporter gene or a gene that confers a selective advantage under the transcriptional control of a transcriptional regulatory region of the transcriptional regulatory region of claim 1 and;

regeneration of said regenerable cultures or tissue segments into mature plants; whereby a transgenic plant that demonstrates green tissue-preferred gene expression of said reporter gene or said gene that confers a selective advantage gene product of said transgene is generated.

6. A method of determining green-tissue preferred gene expression within a transgenic plant comprising:

transformation of regenerable cultures or tissue segments with a transgene comprising a reporter or a gene that confers a selective advantage under the transcriptional control of a transcriptional regulatory region of the transcriptional regulatory region of claim 1 and;

regeneration of said regenerable cultures or tissue segments into mature plants, and;

harvest of samples of certain regions of said mature plant, and; assay of said samples of said certain regions of said mature plant for the presence of an assayable product; whereby the ability of said transcriptional regulatory region to direct green tissue-preferred gene expression is determined by detection of said assayable product in said samples of said certain regions of said mature plant.

7. The method of claim 5 or 6 wherein said regenerable cultures are maize or regenerable maize Hi-II callus cultures.

8. The method of claim 5 or 6 wherein said tissue segments are maize zygotes, embryos, axillary buds, leaf bases, immature ears or immature tassels.

9. A fertile transgenic plant comprising an isolated transcriptional regulatory region of claim 1 that has been transformed into the plant.

10. The fertile transgenic plant of claim 9 wherein the transcriptional regulatory region is that shown in SEQ ID NO: 3 or SEQ ID NO: 5.

11. The fertile transgenic plant of claim 9, wherein the plant is selected from the group consisting of corn, soybean, sunflower, sorghum, alfalfa, wheat, rice and cotton.

12. A vector comprising a DNA molecule of claim 1.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 1207 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: join(12..197, 291..905)

(xi) SEQUENCE DESCRIPTION: SEQ ID NO:1:

```
GAATTCCGTT C CTG TCG GAC TGG TGG AAG AAG GCC CTG GAG AGC GAG AAC        50
             Leu Ser Asp Trp Trp Lys Lys Ala Leu Glu Ser Glu Asn
              1               5                  10
```

```
GTG GAC TCG GTG AAG ATC AGC AAC CGG CTG CAC GAC ACC CCC TGC GTC          98
Val Asp Ser Val Lys Ile Ser Asn Arg Leu His Asp Thr Pro Cys Val
 15              20                  25

GTC GTC ACC TCC AAG TAC GGG TGG AGC GCC AAC ATG GAG AAG ATC ATG         146
Val Val Thr Ser Lys Tyr Gly Trp Ser Ala Asn Met Glu Lys Ile Met
 30              35                  40                  45

CAG GCG CAG ACC CTG TCG GAC TCG AGC AAG CAG GCG TAC ATG CGC GGC         194
Gln Ala Gln Thr Leu Ser Asp Ser Ser Lys Gln Ala Tyr Met Arg Gly
             50                  55                  60

AAA GAGGGCCTCT CGATCGCTCA TCAGTCGCCA GAGGAGTAGT TGATCGAGGT              247
Lys

GAGTGAGGTT GAAAAGCAGG CGGCGAACAA AGGCACCATC GTC ATG GAC GGC GGA         302
                                            Met Asp Gly Gly
                                                         65

TAC TAC GGC GGC CGC GAT CAG CGC TAC AGC GGC GGG TAC TAC GGC GGC         350
Tyr Tyr Gly Gly Arg Asp Gln Arg Tyr Ser Gly Gly Tyr Tyr Gly Gly
             70                  75                  80

GGT GGC ATC GCG ACG CCG GGG TAC GCT CCG GCG GTC CCG TAC GGG ATG         398
Gly Gly Ile Ala Thr Pro Gly Tyr Ala Pro Ala Val Pro Tyr Gly Met
             85                  90                  95

TCG CAG GTG AAC ATC GAG GGC AAC GGG TGC GGG CGG GCG CTG CCG CCG         446
Ser Gln Val Asn Ile Glu Gly Asn Gly Cys Gly Arg Ala Leu Pro Pro
100                 105                 110

CAG CCG ACC GTG AAG GTG TAC TGC CGC GCC AAC CCC AAC TAC GCC ATG         494
Gln Pro Thr Val Lys Val Tyr Cys Arg Ala Asn Pro Asn Tyr Ala Met
115             120                 125                 130

AGC GTC CGC GAC GGG AAG GTG GTG CTG GCG CCG GCG AAC CCC AAG GAC         542
Ser Val Arg Asp Gly Lys Val Val Leu Ala Pro Ala Asn Pro Lys Asp
            135                 140                 145

GAG TAC CAG CAC TGG ATC AAG GAC ATG CGG TGG AGC ACG AGC ATC AAG         590
Glu Tyr Gln His Trp Ile Lys Asp Met Arg Trp Ser Thr Ser Ile Lys
            150                 155                 160

GAC GAG GAA GGT TAC CCG GCG TTC GCG CTG GTG AAC AAG GCG ACC GGG         638
Asp Glu Glu Gly Tyr Pro Ala Phe Ala Leu Val Asn Lys Ala Thr Gly
            165                 170                 175

GAG GCC ATC AAG CAC TCG CTG GGG CAG TCC CAC CCG GTG CGC CTG GTG         686
Glu Ala Ile Lys His Ser Leu Gly Gln Ser His Pro Val Arg Leu Val
180                 185                 190

CCC TAC AAC CCG GAC TTT TTG GAC GAG TCG GTG CTG TGG ACG GAG AGC         734
Pro Tyr Asn Pro Asp Phe Leu Asp Glu Ser Val Leu Trp Thr Glu Ser
195                 200                 205                 210

CGC GAC GTC GGC AAC GGC TTC CGC TGC GTC CGC ATG GTC AAC AAC ATC         782
Arg Asp Val Gly Asn Gly Phe Arg Cys Val Arg Met Val Asn Asn Ile
            215                 220                 225

TAC CTC AAC TTC GAC GCC CTC CAC GGC GAC AAG TGG CAC GGC GGC GTC         830
Tyr Leu Asn Phe Asp Ala Leu His Gly Asp Lys Trp His Gly Gly Val
            230                 235                 240

CGT GAC GGC ACC GAC GTC GTG CTC TGG AAG TGG TGC GAG GGC GAC AAC         878
Arg Asp Gly Thr Asp Val Val Leu Trp Lys Trp Cys Glu Gly Asp Asn
            245                 250                 255

CAG CGC TGG AAG ATC CAG CCC TAC TAC TGAACCAACG GATGATATGA              925
Gln Arg Trp Lys Ile Gln Pro Tyr Tyr
            260                 265

CCATCGCGCC CATCGATCGT GCACATGCAT GCATACGTAC TAGCAGAATA ACAGGGGTCT       985

TATCTCCCGA GGCGTCTTTT GCATGCATGC CAGCAGTTGC ATAGATAAAG CAGGAGCGAG      1045

ACAAAGGGTG TTCATGTATA TTGCAGCTGT ATCACTGTAT GTATGTGCCA TTGTGCCTTG      1105

TAATAATACA TATAATAATA AAGTTGCTCG GAAAAAAAAA AAAAAAAAA AAATCTAGAG       1165

TCGACCTGCA GCCCAAGCTT GTATTCTATA GTGTCACCTA AA                        1207
```

(2) INFORMATION FOR SEQ ID NO:2:

(i) SEQUENCE CHARACTERISTICS:
        (A) LENGTH: 267 amino acids
        (B) TYPE: amino acid
        (D) TOPOLOGY: linear (ii) MOLECULE TYPE: protein (xi) SEQUENCE DESCRIPTION: SEQ ID NO:2:

```
Leu Ser Asp Trp Trp Lys Lys Ala Leu Glu Ser Glu Asn Val Asp Ser
 1               5                  10                  15

Val Lys Ile Ser Asn Arg Leu His Asp Thr Pro Cys Val Val Thr
             20                  25                  30

Ser Lys Tyr Gly Trp Ser Ala Asn Met Glu Lys Ile Met Gln Ala Gln
             35                  40                  45

Thr Leu Ser Asp Ser Ser Lys Gln Ala Tyr Met Arg Gly Lys Met Asp
         50                  55                  60

Gly Gly Tyr Tyr Gly Gly Arg Asp Gln Arg Tyr Ser Gly Gly Tyr Tyr
65                  70                  75                  80

Gly Gly Gly Gly Ile Ala Thr Pro Gly Tyr Ala Pro Ala Val Pro Tyr
                 85                  90                  95

Gly Met Ser Gln Val Asn Ile Glu Gly Asn Gly Cys Gly Arg Ala Leu
                100                 105                 110

Pro Pro Gln Pro Thr Val Lys Val Tyr Cys Arg Ala Asn Pro Asn Tyr
            115                 120                 125

Ala Met Ser Val Arg Asp Gly Lys Val Val Leu Ala Pro Ala Asn Pro
130                 135                 140

Lys Asp Glu Tyr Gln His Trp Ile Lys Asp Met Arg Trp Ser Thr Ser
145                 150                 155                 160

Ile Lys Asp Glu Glu Gly Tyr Pro Ala Phe Ala Leu Val Asn Lys Ala
                165                 170                 175

Thr Gly Glu Ala Ile Lys His Ser Leu Gly Gln Ser His Pro Val Arg
            180                 185                 190

Leu Val Pro Tyr Asn Pro Asp Phe Leu Asp Glu Ser Val Leu Trp Thr
        195                 200                 205

Glu Ser Arg Asp Val Gly Asn Gly Phe Arg Cys Val Arg Met Val Asn
210                 215                 220

Asn Ile Tyr Leu Asn Phe Asp Ala Leu His Gly Asp Lys Trp His Gly
225                 230                 235                 240

Gly Val Arg Asp Gly Thr Asp Val Val Leu Trp Lys Trp Cys Glu Gly
                245                 250                 255

Asp Asn Gln Arg Trp Lys Ile Gln Pro Tyr Tyr
                260                 265
```

(2) INFORMATION FOR SEQ ID NO:3:

(i) SEQUENCE CHARACTERISTICS:
        (A) LENGTH: 1997 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1928..1996

(xi) SEQUENCE DESCRIPTION: SEQ ID NO:3:

-continued

```
TACCGGGCCC CCCCTCGAGG TCGACGGTAT CGATAAGCTT GATATCGAAT TCTAACTCAA    60

ACGAACATGC CCTTATCGAT TTAGCTAGAG AGATGCGAGG AAAACTCTTA TTAGTATTGT   120

TGCTTTGGTG GTGGCGTAGA TAAAATAGAG CAAATAGAAA GGCACATCAG AGGTGGCACT   180

GGAGACGATG TTGACAGTGG CGTCGCACTT CCTCTCGAAG CTCGACCATG CCTGGCAGCA   240

CAACGTGTAT GACCCGCATG ACGCCCTCGA CGTTGACCTA GATCAGTTGC GCAGCAGCTC   300

CTCATCCACC CCGTGCCAGT AGTGCGCGTA CGGATAAGAC AACCCATCAT AGCCATGGAT   360

GGAGTCTCGA GCATCTCGAC GCCGGCCACC AGCCCCTCGA GATCCTTGCT GGAGGCGCGG   420

GCGTCGAGGA GGAGGAGATG GGCGAAGGTG AGGGAGGGGA CCAAGGGGGT CTATCGCGGT   480

AGGACAGGGG GCCAGGAAGG CAGGGCAAC ACATGGGGGC AGCACAAGCA GGGGCCGGAG   540

TGGAGGGAGG CAAGGATGGT AGGCGTTTGG CGTCGCAAGG GAGGCGAGGA GCGCGGTGCA   600

GCGGTGCATG GAACGCGGGA TGGGCTTGCG ACTGACGATG GCGTGGAGGG ACGACATCAG   660

TATAGATGGC CAAATGGGTC GTACCTATCA GACTGGCCTG AAGTACGAAC CATTTAATAG   720

TGTCGTGGCC CAACCTGACA TTATTAAAAT GGGCTCGTGC CAGCACGGCA CGAGAGGCGT   780

GCCATGCTTG AGCCGTTGTC TCGGCCCGTA GTGCCGGTTT GGCCTAATAT GATTATTTTT   840

TTATTATTTT GAAAACTCAG CCGACACATA TTTATAACAC CTATTGACTA TTAGGCACAA   900

ACTTGATTGG GCTCAAGTGG GTAGCAGAGC ATAGTCAGTG TCTGTTGCCT TTACCAAGGC   960

GCACGGGTTT GATCCCCCTC CCTGCGCTAT AATTTTGGAC TATTTTTCTA TAGGCGTCGA  1020

GACGAAGCAT GATTCCACCA GTGATCTACA CTATTATCTT AATATGTAGT AGAGATAGAG  1080

ATTTTATAGA TTCAGACCCC TAAACCTTTA ATGAGATTAT TTTTCTCAGC TACTCAAATA  1140

AAGGGGAGAA CTCTCCTCCC CAATTAACCG TTTTTTTCTT CATATTTTCT ACACTACATA  1200

TGCCTAAAAT AAATAATTGA GAGATGAGTT AAGAGAAAGA AAAGGTAATG TATAATGCTG  1260

GTTTTCAGGA TGGTTGGTTT TAAGATCTAA TTGTTATTAT TCACCGCCTA AACGAACCTT  1320

TAAAATAAGA CATAACACAG CTCCTTAATT TCTCATTGGG CATGGAGTTT TCTTGTTTTG  1380

CTGGAGAGAA AGAAGACCTT TGAAATTTCA AAACACTCTT TTGTGGCTAG TTTGAAAACT  1440

CGAATCATCT CCAGGATCGA CCGGAATTAG GGAATAAATA AACTATTTTT TCTCTCAATC  1500

TCAAAGACAA TTTAAGTTTC CAAACTAGCG ATTAATCTTA ACCAATGACT AGACTTTGTG  1560

TTGGTTTTTT CTCTTACTGC TGGAGATGCT AAGGATTCTT CTTCCAAGAA CGACTAGAAA  1620

CCGAATCGCT TTTTCCCTCG GCTAGTTTCG CATGGCATCG TCCTTCCTGC CCATGCGCGC  1680

ACAACCATCC ATCCACTGAC GATGCGATGC CTACCCACCA CCTCGCGCAG CGTGATGCTA  1740

ACGCCACCAC ATGCACCACC AGTGGGGCAG CTGGGGACGC CGGGAGCAAC CGGCAGCGCC  1800

CTATAAATCT GCCGGCCCGG CCGTTGCATT GTCTGCGTCA GGGCCTCTTG ATCATCAGTC  1860

GCCAGAGGAG CTGTTGATCG AGGTGAGTGA GGTTGAAAAG CAGGCGGCGA ACAAAGGCAC  1920

CATCGTC ATG GAC GGC GGA TAC TAC GGC GGC CGC CAC CGC GGT GGA GCT    1969
        Met Asp Gly Gly Tyr Tyr Gly Gly Arg His Arg Gly Gly Ala
          1               5                  10

CCA GCT TTT GTT CCC TTT AGT GAG GGT T                              1997
Pro Ala Phe Val Pro Phe Ser Glu Gly
 15              20
```

(2) INFORMATION FOR SEQ ID NO:4:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Gly Gly Tyr Tyr Gly Gly Arg His Arg Gly Gly Ala Pro Ala
 1               5                  10                  15
Phe Val Pro Phe Ser Glu Gly
            20
```

(2) INFORMATION FOR SEQ ID NO:5:

(i) SEQUENCE CHARACTERISTICS:
        (A) LENGTH: 1033 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CCGGTTAACT CTAGAGGGTA GCAGAGCATA GTCAGTGTCT GTTGCCTTTA CCAAGGCGCA      60
CGGGTTTGAT CCCCCTCCCT GCGCTATAAT TTTGGACTAT TTTTCTATAG GCGTCGAGAC     120
GAAGCATGAT TCCACCAGTG ATCTACACTA TTATCTTAAT ATGTAGTAGA GATAGAGATT     180
TTATAGATTC AGACCCCTAA ACCTTTAATG AGATTATTTT TCTCAGCTAC TCAAATAAAG     240
GGGAGAACTC TCCTCCCCAA TTAACCGTTT TTTTCTTCAT ATTTTCTACA CTACATATGC     300
CTAAAATAAA TAATTGAGAG ATGAGTTAAG AGAAAGAAAA GGTAATGTAT AATGCTGGTT     360
TTCAGGATGG TTGGTTTTAA GATCTAATTG TTATTATTCA CCGCCTAAAC GAACCTTTAA     420
AATAAGACAT AACACAGCTC CTTAATTTCT CATTGGGCAT GGAGTTTTCT TGTTTTGCTG     480
GAGAGAAAGA AGACCTTTGA AATTTCAAAA CACTCTTTTG TGGCTAGTTT GAAAACTCGA     540
ATCATCTCCA GGATCGACCG GAATTAGGGA ATAAATAAAC TATTTTTTCT CTCAATCTCA     600
AAGACAATTT AAGTTTCCAA ACTAGCGATT AATCTTAACC AATGACTAGA CTTTGTGTTG     660
GTTTTTTCTC TTACTGCTGG AGATGCTAAG GATTCTTCTT CCAAGAACGA CTAGAAACCG     720
AATCGCTTTT TCCCTCGGCT AGTTTCGCAT GGCATCGTCC TTCCTGCCCA TGCGCGCACA     780
ACCATCCATC CACTGACGAT GCGATGCCTA CCCACCACCT CGCGCAGCGT GATGCTAACG     840
CCACCACATG CACCACCAGT GGGGCAGCTG GGGACGCCGG GAGCAACCGG CAGCGCCCTA     900
TAAATCTGCC GGCCCGGCCG TTGCATTGTC TGCGTCAGGG CCTCTTGATC ATCAGTCGCC     960
AGAGGAGCTG TTGATCGAGG TGAGTGAGGT TGAAAAGCAG GCGGCGAACA AAGGCACCAT    1020
CGCCATGGAC GGC                                                      1033
```

(2) INFORMATION FOR SEQ ID NO:6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:6:

```
CCGGTTAACT CTAGAGGGTA GCAGAGCATA GTCAGTG                              37
```

(2) INFORMATION FOR SEQ ID NO:7:

(i) SEQUENCE CHARACTERISTICS:

(A) LENGTH: 21 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Oligonucleotide"

(xi) SEQUENCE DESCRIPTION: SEQ ID NO:7:

GCCGTCCATG GCGATGGTGC C                                        21